United States Patent
Takeuchi et al.

[19]

[11] Patent Number: 5,942,616
[45] Date of Patent: Aug. 24, 1999

[54] METAL ION COORDINATED COMPLEX CRYSTAL

[75] Inventors: Hisato Takeuchi, Chita; Azusa Tsukigase, Chiryu; Arimitsu Usuki, Nagoya, all of Japan

[73] Assignee: Kabushiki Kaisha Toyota Chuo Kenkyusho, Aichi-ken, Japan

[21] Appl. No.: 08/633,021

[22] Filed: Apr. 16, 1996

[30] Foreign Application Priority Data

Apr. 17, 1995 [JP] Japan .................................. 7-090979

[51] Int. Cl.⁶ .............................. C07F 1/08; C07F 15/02; C07F 15/04
[52] U.S. Cl. ................................ 544/225; 546/2; 546/10; 546/12
[58] Field of Search .................... 546/2, 10, 12; 544/225

[56] References Cited

U.S. PATENT DOCUMENTS 5,393,606  2/1995  Chetcuti ................................ 428/332

FOREIGN PATENT DOCUMENTS 54-8183  1/1979  Japan .

OTHER PUBLICATIONS

CA 106(18):148285z, R. Vicente, et al.
Tebbe, Chem Abs 125, 236899a (1996).
Luo, Chem Abs 113, 223345 (1989).
Hodges, Inog Chem 14, 525 (1975).
Vicento, Polyhedron 5, 2033 (1986).

*Primary Examiner*—Mark L. Berch
*Attorney, Agent, or Firm*—Oblon, Spivak, McCleLLand, Maier & Neustadt, P.C.

[57] ABSTRACT

A metal ion coordinated complex crystal is composed of cation of a nitrogen-containing heterocyclic aromatic compound, anion of triiodine and metal ion. The complex crystal can be used as light-polarizing particles having a stable and strong polarizability which is resistant to ultra violet, an excellent heat resistance, excellent moisture resistance and excellent insolubility.

29 Claims, 4 Drawing Sheets

METAL ION COORDINATED COMPLEX CRYSTAL

BACKGROUND OF THE INVENTION

1. Field of the Invention

The present invention relates to a metal ion coordinated complex crystal which is suitable for use as light-polarizing particles for a light-adjusting component of a light valve or a light-adjusting glass, and which is composed of a cation of a nitrogen-containing heterocyclic aromatic compound, an anion of triiodine and a metal ion.

2. Description of the Related Art

Conventionally, one light-adjusting component performs its function by dispersing light-polarizing particles into a dispersion medium, and making them orient in the dispersion medium in response to an electric field. Another light-adjusting component has a function of controlling optical properties (light-transmitting and light-screening performance) of the dispersion medium by randomizing the light-polarizing particles in it. It is proposed in Japanese Unexamined Patent Publication No. 144893/1978 that a complex compound such as dihydrocinchonidine periodide compound is used as light-polarizing particles. When the light-polarizing particles are used for a light-adjusting component, a dispersion medium containing the light-polarizing particles is filled between a pair of transparent electrodes coating inner surface of a pair of transparent substrates. The dispersion medium may be filled into a micro cell in order to improve optical properties or safety of the light-adjusting component.

The above-mentioned dispersion medium containing the light-polarizing particles usually contains moisture. The molecules of water destroy a clathlate structure of a complex such as above-mentioned periodide compound, and resultantly polarizability of the dispersion deteriorates. However, the conventional light-polarizing particles have poor moisture resistance. A light-polarizing particle with excellent moisture resistance has to be developed in order to obtain durability and stability of a light-adjusting component.

As automobiles have been improved their performance, it is desired that a windshield glass can screen a light. Therefore, it is necessary to manufacture a light-screening glass using light-polarizing particles. When a light-screening glass is formed of a light-adjusting component comprising the above-described light-polarizing particles, a dispersion medium containing the light-polarizing particles should be sealed between a laminated glass in the middle stage of manufacturing the laminated glass. However, the light-polarizing particles deteriorate or decompose when they are exposed to a temperature above 100° C. Therefore, the light-polarizing particles are not suitable for use as the laminated glass for automobiles which is produced at a temperature above 130° C.

Thus, in case that the light-adjusting component is used for outer parts of automobiles or outer materials of houses, the light-adjusting component exposes to a more severe condition. As a result, it is required to use light-polarizing particles which have more excellent durability than conventional ones. In order to obtain a long-lived light-adjusting component, it is required to provide a complex crystal which shows excellent heat resistance, excellent moisture resistance and excellent insolubility.

In order to meet the above conditions, the present inventors previously filed Japanese Patent Application (Japanese Unexamined Patent Publication No. 17473/1993 and Japanese Unexamined Patent Publication No. 357199/1992) concerning heat resistant herapathite as a complex crystal which can be used as red light-polarizing particles. Subsequently, the inventors filed Japanese Patent Application (Japanese Patent Application No. 329115/1991, Japanese Patent Application No. 325592/1992 and Japanese Patent Application No. 187020/1992) concerning phenanthroline compound, which is tricyclic fused compound having a nitrogen atom as a fused ring member for blue light-polarizing particles. The complex crystal such as phenanthroline compound has the same effect as that of the complex crystal such as herapathite. However, if it is required to use a complex crystal which have further durability and heat resistance, the above complex crystal of phenanthroline compound are not enough to satisfy such durability and weather resistance.

SUMMARY OF THE INVENTION

Accordingly, it is an object of the present invention to provide a complex crystal which is suitable for use as light-polarizing particles having ultra-violet resistance and excellent durability.

A metal ion coordinated complex crystal according to the present invention is characterized in that it is composed of a cation of a nitrogen-containing heterocyclic aromatic compound, an anion of triiodine and a metal ion.

Preferably, the nitrogen-containing heterocyclic aromatic compound has a substituent on an aromatic ring thereof, and it is a polycyclic compound comprising at least one aromatic ring.

More preferably, the nitrogen-containing heterocyclic aromatic compound has at least one nitrogen atom as a ring member of the aromatic ring or the substituent.

The nitrogen-containing heterocyclic aromatic compound may have at least one fused aromatic ring.

More preferably, the nitrogen-containing heterocyclic aromatic compound has a fused aromatic ring system comprising 3 to 5 rings.

The complex crystal can be used as light-polarizing particles having stable and strong polarizability which is ultra-violet resistance, excellent heat resistance, excellent moisture resistance and excellent insolubility.

The above complex crystal is formed as follows.

Two kinds of solutions are prepared: One is the solution of a metal sulfate and a triiodine ion, and the other is the solution of a nitrogen-containing heterocyclic aromatic compound neutralized with an acid. These solutions are mixed at once, then, filtered a precipitated crystal. The obtained precipitated crystal is a charge-transfer complex crystal in which ions of a nitrogen-containing heterocyclic aromatic compound are coordinated with ions of triiodine and metal ions. Refer to FIG. 2 as one of examples to understand the configuration of the complex crystal.

"Charge-transfer" is defined as that the process in which an ion takes an electron from a neutral atom, with a resultant transfer of charge. "Charge-transfer" complexes are defined as that compounds in which electrons move between molecules.

The structure of the complex crystal is supposed as follows. A charge-transfer complex is formed between an ionized nitrogen-containing heterocyclic aromatic compound and an anion of triiodine, in which a metal ion is coordinated with a part of nitrogen-containing heterocyclic aromatic compound, thereby forming the complex crystal. The amount of a metal ion in the complex crystal can be adjusted in accordance with the amount of a metal ion in the above mixed solution. The amount of a metal ion is in the range of from 0.01 to 15 atomic % with respect to the complex crystal, preferably, of from 0.1 to 5 atomic % and more preferably of from 0.5 to 3.5 atomic %.

The metal ion bridges between two columnar charge-transfer complexes to fix them. So, the metal ion coordinated complex crystal not only maintains the property which belongs to the complex crystal without containing a metal ion but also shows new properties such as weather resistance.

It is preferable that metal ion to be coordinated with complex crystal is ion of transition metals, specifically, copper, iron or nickel.

A nitrogen-containing heterocyclic aromatic compound may include a plurality of aromatic rings being unified and having one side in common, for example, naphthalene in which two benzene rings are fused.

As for the nitrogen-containing heterocyclic aromatic compound according to the present invention, it is preferable that the number of aromatic fused rings is more than that of naphthalene, that is, the number of aromatic fused rings is not less than 3. Furthermore, the nitrogen-containing heterocyclic aromatic compound has at least one nitrogen atom in its molecule. In the nitrogen-containing heterocyclic aromatic compound, a nitrogen atom may constitute the above heterocyclic rings (for example, a pyridine ring or a pyrazine ring), or it may be combined as a substituent on the heterocyclic aromatic rings. It is preferable that the nitrogen atom constitutes the heterocyclic rings. In this case, it is possible to obtain more excellent efficiency in converting light energy received at aromatic fused rings into thermal energy due to metal ion.

The above heterocyclic rings may contain a sulfur atom or an oxygen atom.

The number of aromatic fused rings is at least 3, and preferably, tricyclic, tetracyclic or pentacyclic. In such a nitrogen-containing heterocyclic aromatic compound, a conjugate system extends and a molecular weight increases. Furthermore, when the number of aromatic fused rings increases, the molecular structure becomes rigid. At the same time, the polarizability of the heterocyclic rings containing an atom other than carbon becomes high, and the heterocyclic rings are less dissolved into the dispersion medium having low polarizability such as ditridecyl phthalate. In the complex crystal comprising the above nitrogen-containing heterocyclic aromatic compound, an expansive plane of the nitrogen-containing heterocyclic aromatic compound covers an anion of triiodine and protects a complex crystal from an attack of water, oxygen or the solvent. In other words, an expansive plane of the nitrogen-containing heterocyclic aromatic compound stereochemically stabilizes the whole atoms. Therefore, the complex crystal improves its stability, heat resistance, moisture resistance and insolubility. A nitrogen atom of the compound works as an active site for producing a complex crystal.

Ionized triiodine ($I_3^-$) forms a complex with a conjugated system of the nitrogen-containing heterocyclic aromatic compound and a nitrogen. The complex crystal according to the present invention has a structure in which molecules of a nitrogen-containing heterocyclic aromatic compound and chains of $I_3^-$ are disposed uniformly and orderly. Molecular planes of the nitrogen-containing heterocyclic aromatic compound may be parallel each other. The complex crystal may have a clathlate structure.

The light-polarizing particles are used for a light valve or a light-adjusting glass, and they have light-screening performance and polarizability. The amount of light-screening, or polarizability can be adjusted, such as, by applying voltage. The light-polarizing particles according to the present invention have polarization, so they can be oriented by applying an external electric field. Furthermore, the light-polarizing particle has an acicular or a planar crystal structure. When the light-polarizing particles are dispersed randomly, they can screen a light. When the light-polarizing particles are oriented, they can transmit a light.

The complex crystal according to the present invention has polarizability by means of $I_3^-$ contained in the complex crystal. Furthermore, the complex crystal has polarization by means of an interaction between the nitrogen-containing heterocyclic aromatic compound and $I_3^-$. Therefore, the complex crystal can be used as light-polarizing particles for a light valve, a light-adjusting glass, a glare-proof mirror, a display component, or a light-adjusting component.

In the complex crystal according to the present invention, the nitrogen atom in the molecule of the nitrogen-containing heterocyclic aromatic compound is neutralized by acid. The complex crystal is composed of the nitrogen-containing heterocyclic aromatic compound which is ionized by adding proton to a nitrogen atom, the anion of triiodine which is formed from a mixture of iodine and potassium iodide, and metal ion which is coordinated with a part of the nitrogen-containing heterocyclic aromatic compound.

As shown in FIG. 1, a metal complex comprising a nitrogen-containing heterocyclic aromatic compound and a metal ion absorbs ultra violet. Then, the absorbed energy is concentrated on a metal ion, and it is emitted as thermal energy outside. So, the metal complex is stable for ultra violet. It is considered that, as shown in FIG. 2, in the complex crystal A according to the present invention, a columnar charge-transfer complex B, which comprises a nitrogen-containing heterocyclic aromatic compound and an anion of periodide, is arranged to be parallel to each other, and a metal ion (M) is coordinated with a part of the nitrogen-containing heterocyclic aromatic compound to form metal complex C. Therefore, in the metal ion coordinated complex crystal, it is possible to convert the irradiated ultra violet into heat. At this time, the complex crystal as a base material is thermally stable, and it never deteriorates its property due to converted heat energy.

The metal ion coordinated in the charge-transfer complex crystal of the present invention never destroys the original properties of the complex crystal. Therefore, it is possible to obtain the complex crystal which is suitable for use as light-polarizing particles having excellent heat resistance, excellent moisture resistance and excellent insolubility.

The complex crystal according to the present invention has a structure in which cations of a nitrogen-containing heterocyclic aromatic compound and chains of anions of triiodine are arranged alternately and orderly. This arrangement provides the complex crystal with polarizability.

As for the complex crystal, an electron placed on a complex unit is likely to move because of an interaction between the cation of a nitrogen-containing heterocyclic aromatic compound and anion of triiodide ($I_3^-$). Therefore, the complex crystal exhibits excellent polarization.

Note that charge-transfer complexes are defined as compounds which electrons move between molecules.

BRIEF DESCRIPTION OF THE DRAWINGS

A more complete appreciation of the present invention and many of its advantages will be readily obtained as the same becomes better understood by reference to the follow

DETAILED DESCRIPTION OF THE PREFERRED EMBODIMENTS

Figure 1:
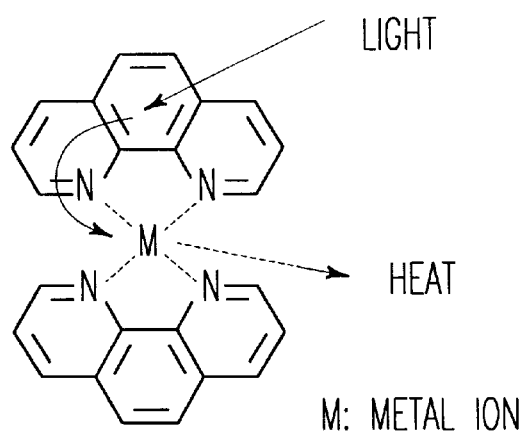
- FIG. 1 is a typical view for explaining that light is converted into heat due to metal ion coordinated complex crystal.
Figures 2B, 2C:
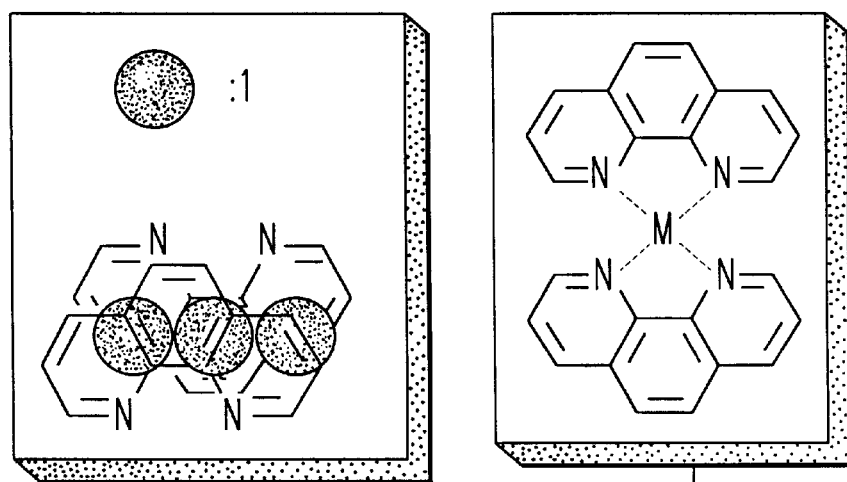
FIG. 2 is a typical view for showing the complex crystal in which metal ion is coordinated.
Figure 2A:
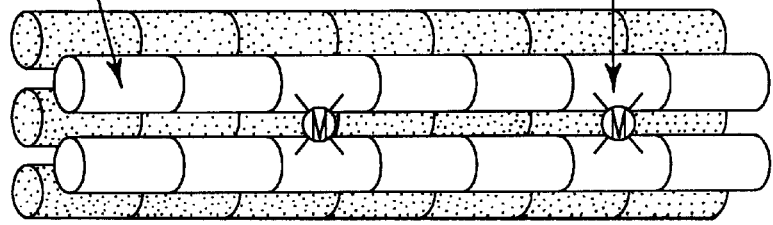
Figure 3:
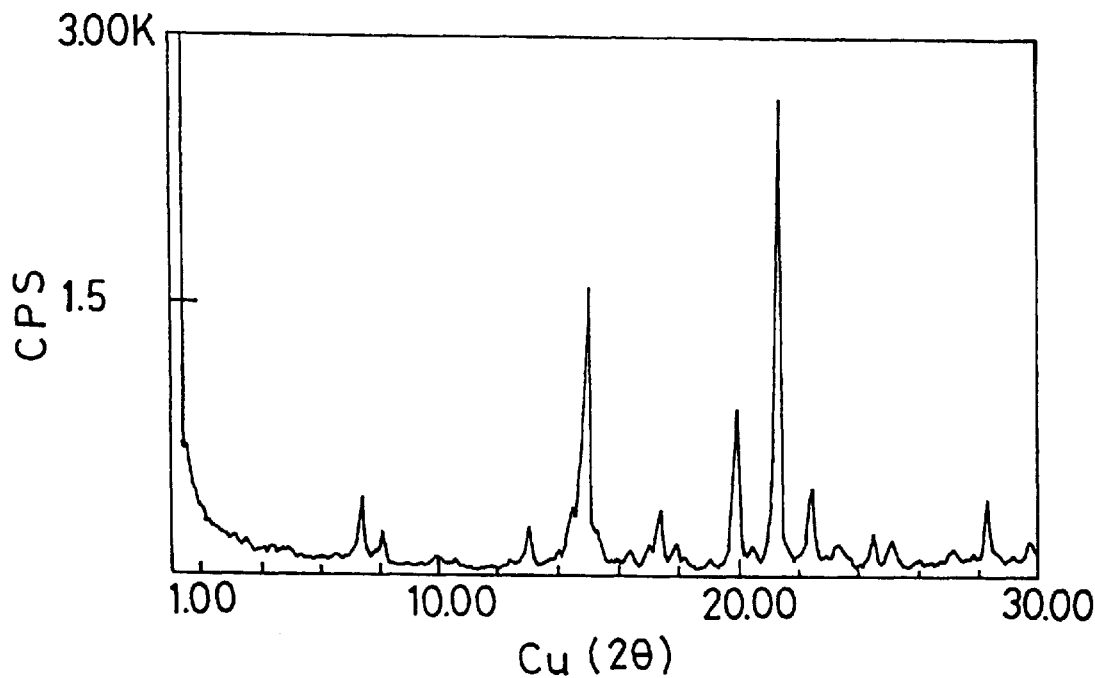
FIG. 3 is an X-ray chart of the complex crystal in the First Preferred Embodiment according to the present invention.
Figure 4:
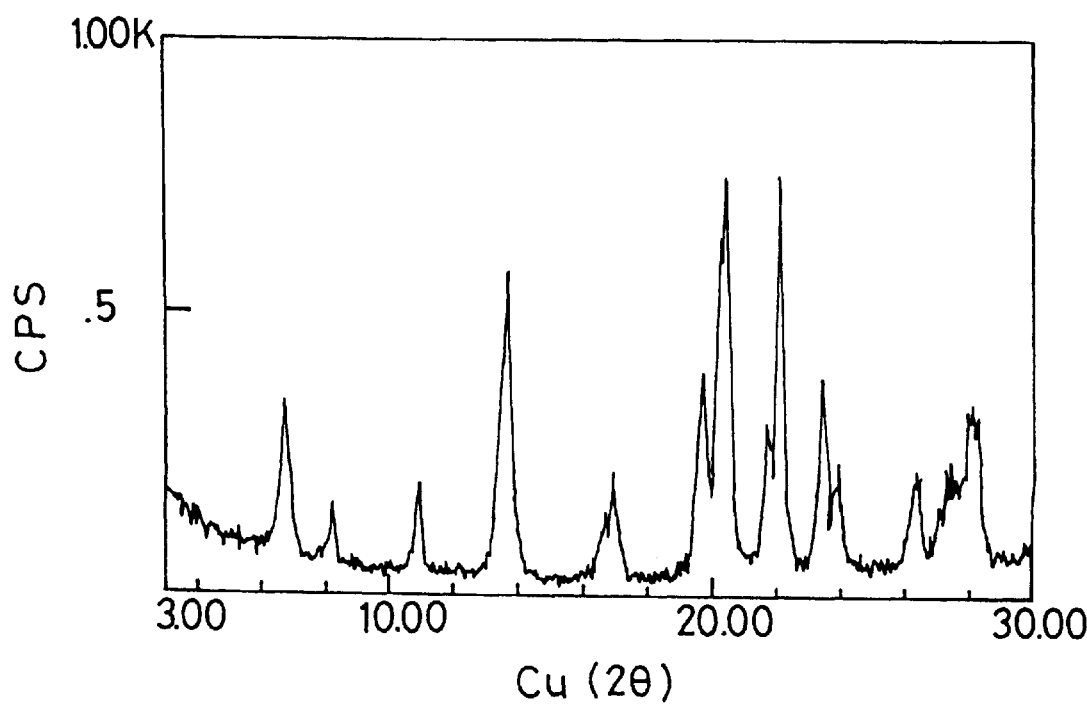
FIG. 4 is an X-ray chart of the complex crystal in the Second Preferred Embodiment according to the present invention.
Figure 5:
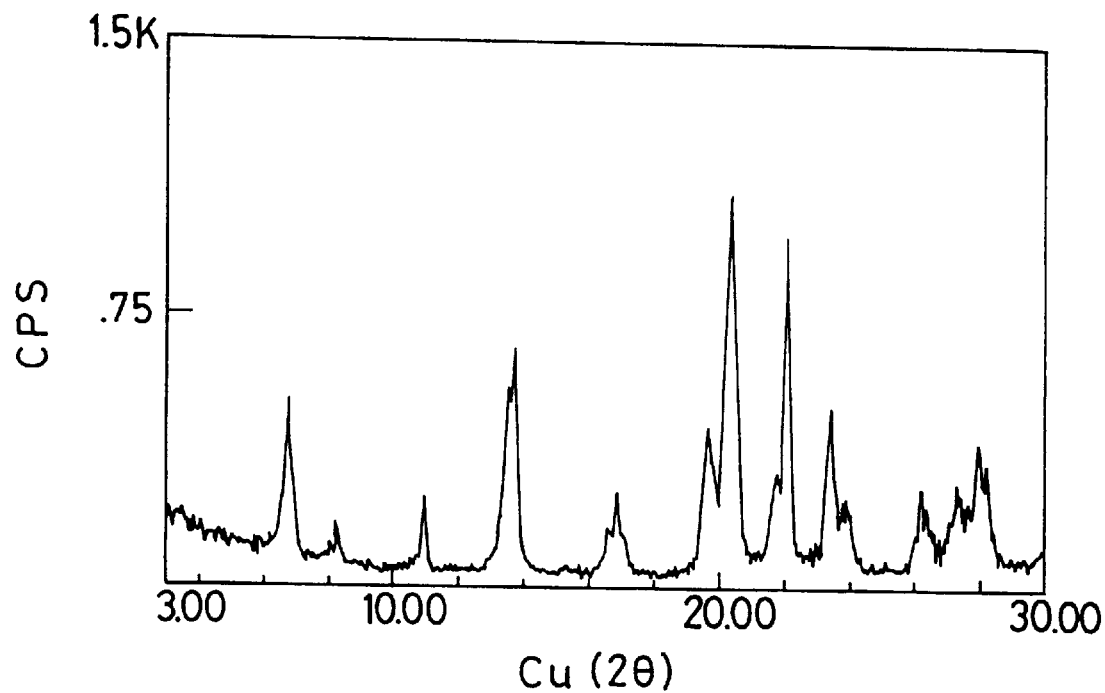
FIG. 5 is an X-ray chart of the complex crystal in the Third Preferred Embodiment according to the present invention.
Figure 6:
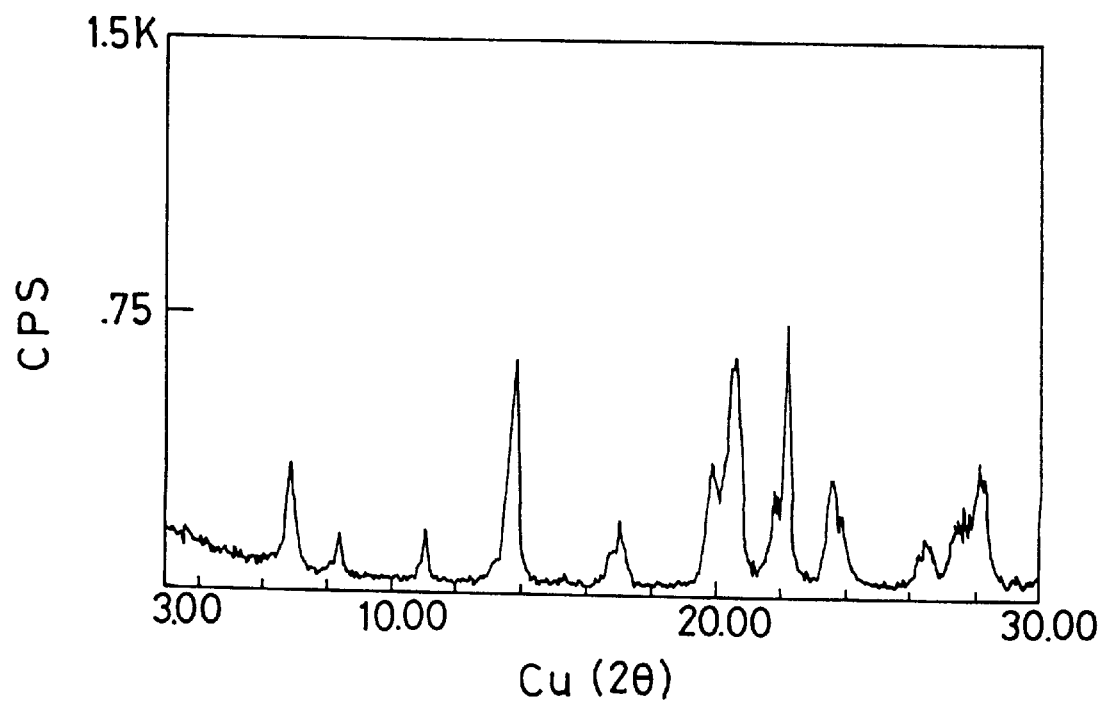
FIG. 6 is an X-ray chart of the complex crystal in the Fourth Preferred Embodiment according to the present invention.

The nitrogen-containing heterocyclic aromatic compound includes 1,10-phenanthroline (shown as structural formula 1), pyrazinophenanthroline (shown as structural formula 2), dipyridophenazine (shown as structural formula 3), 5-methoxyphenanthroline (shown as structural formula 4), 5-aminophenanthroline (shown as structural formula 5), diphenylphenanthroline (shown as structural formula 6), N,N'-ditridecyl-3,4,9,10-perylenetetracarboxylic diimide (shown as structural formula 7), N,N'-Bis(2,6-dimethylphenyl)-3,4,9,10-perylenetetracarboxylic diimide (shown as structural formula 8) and 1,10-phenanthroline derivatives in which a substituent includes at least one selected from the group consisting of amino group, methoxy group, diphenyl group or the like. Structural formulas 2 to 6 are also regarded as 1,10-phenanthroline derivatives. The nitrogen-containing functional group may include an amide group, hydrazide group, imino group or guanidyl group, in addition to an amino group.

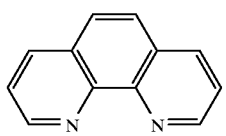

[structural formula 1]

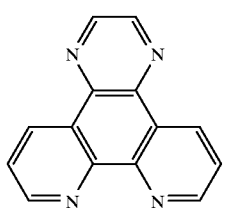

[structural formula 2]

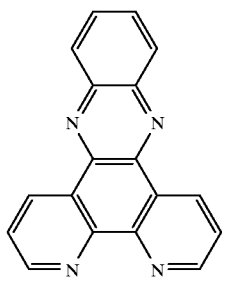

[structural formula 3]

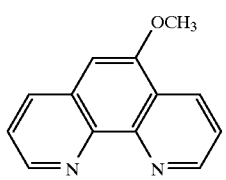

[structural formula 4]

-continued

[structural formula 5]

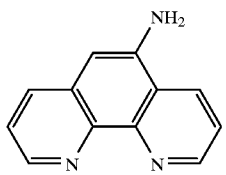

[structural formula 6]

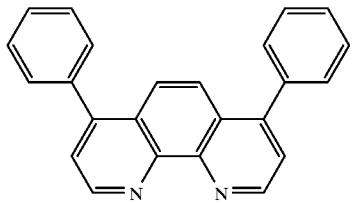

[structural formula 7]

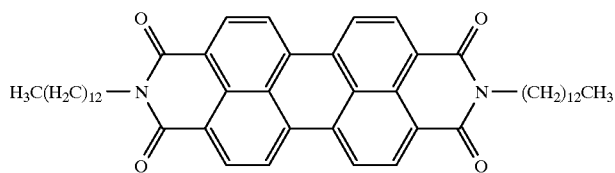

[structural formula 8]

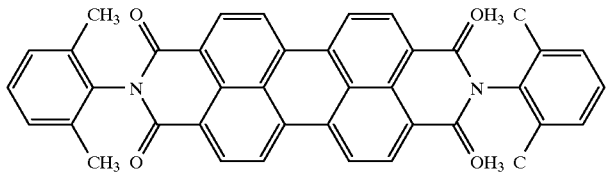

Moreover, the derivatives of the nitrogen-containing heterocyclic aromatic compound may contain a halogen substituent, an aliphatic hydrocarbon substituent having not more than 10 carbons, an aromatic hydrocarbon substituent, an alkoxy, and thioether substituents. These substituents binded by way of sulfur or oxygen to the heterocyclic aromatic compound, for example, include a methoxy group, ethoxy group, phenoxy group, methylthio group, ethylthio group, or phenylthio group.

Concerning the above-described substituents, when the number of carbons on the substituents are more than 10, the complex crystal deteriorates its stability, heat resistance and moisture resistance.

In this complex crystal, it is considered that the nitrogen-containing heterocyclic aromatic compound is positively charged (cation), and iodine is charged negatively (anion). Therefore, when a substituent having an electron donativity is combined with the aromatic ring, it stabilizes the positively charged aromatic ring, and improves heat resistance of the complex crystal.

The complex crystal according to the present invention may include an acid ion as one of the structural elements. The acid contained in the complex crystal neutralizes basicity of a nitrogen atom contained in the nitrogen-containing heterocyclic aromatic compound to form a neutral salt. The acid may be an inorganic acid or an organic acid. The inorganic acid, for example, is a proton, hydrochloric acid, sulfuric acid, phosphoric acid, or hydroiodic acid. The organic acid, for example, is a sulfonic acid such as a benzenesulfonic acid, toluenesulfonic acid, or methanesulfonic acid; monocarboxylic acid such as an acetic acid, propionic acid, butyric acid, valeric acid, trifluoroacetic acid, or benzoic acid; or dicarboxylic acid such as an oxalic acid, malonic acid, maleic acid, fumaric acid, or phthalic acid.

The complex crystal according to the present invention may include an anion of acid as one of the structural elements.

The acid ion suitable for forming the complex crystal as light-polarizing particles is desirably sulfonic acid ion or dicarboxylic acid ion.

Having generally described the present invention, a further understanding can be obtained by reference to the specific preferred embodiments which are provided herein for purposes of illustration only and are not intended to limit the scope of the appended claims.

The Preferred Embodiments according to the present invention will be hereinafter described with reference to FIGS. 1 through 7.

First Preferred Embodiment

A First Preferred Embodiment employed 1,10-phenanthroline to obtain a metal ion coordinated complex crystal as follows.

1.01 g (5.6 millimol) of 1,10-phenanthroline (shown as structural formula 1) was dissolved into a mixed solution comprising 21 g of water and 0.137 g of concentrated sulfuric acid and stired to prepare a solution (A). 0.711 g of iodine, 0.465 g of potassium iodide and 8.9 mg of copper sulfate (1 mol % per 1,10-phenanthroline) were dissolved into a mixed solution comprising 15.0 g of water and 3.5 g of ethanol and stirred to prepare a solution (B). The solutions (A) and (B) were mixed at once and stirred for 1 hour to form a precipitate. The precipitate was filtered and then vacuum dried to obtain a metal ion coordinated complex crystal.

The complex crystal was identified to contain 0.18 atomic % of copper ion with respect to 1,10-phenanthroline by means of a high-frequency plasma emission spectral analysis method. The crystal was identified as a complex crystal comprising 1,10-phenanthroline, the anion of triiodine and the copper ion by means of an X-ray diffraction (shown as FIG. 3), Elementary analysis, Raman spectrum and Infrared absorption spectrum. The complex crystal comprised 7 parts of the cation of 1,10-phenanthroline, 3 parts of $I_3^-$, and 0.06 parts of the metal ion. 0.1 g of the obtained complex crystal and 0.1 g of cellulose nitrate were dissolved into a mixed solution comprising 7 g of acetone and 10 g of ethanol to prepare a solution. 10 g of ditridecyl phthalate (DTDP) was added to the solution, and aceton and ethanol were distilled under reduced pressure to precipitate a microcrystal of the complex in DTDP. The DTDP solution was treated by the ultrasonic cleaner for 10 hours, and after that, remaining aceton and ethanol were removed under reduced pressure. Particles which were not refined satisfactorily were precipitated and removed by a centrifugal separation treatment (18,000 rpm, 20 minutes), thereby obtaining a blue suspension in which the complex crystal was dispersed into DTDP.

The blue suspension was sealed in glass cell having a gap of 100 μm, and tested for a weather resistance by a sunshine weather-O-meter for 240 hours. As a result, the color and the dispersed state of the blue suspension never changed.

Second Preferred Embodiment

A Second Preferred Embodiment employed pyrazino phenanthroline to obtain a metal ion coordinated complex crystal as follows. 1.30 g (5.6 millimol) of pyrazinophenanthroline (shown as structural formula 2) was dissolved into a mixed solution comprising 36 g of water and 0.13 g of concentrated sulfuric acid and stirred to prepare a solution (A). 0.711 g of iodine, 0.465 g of potassium iodide and 8.5 mg of iron sulfate (1 mol % per pyrazino phenanthroline) were dissolved into a mixed solution comprising 15.0 g of water and 3.5 g of ethanol and stirred to prepare a solution (B). The solutions (A) and (B) were mixed at once and stirred for 1 hour to form a precipitate. The precipitate was filtered and then vacuum dried to obtain a metal ion coordinated complex crystal.

The complex crystal was identified to contain 0.17 atomic % of iron ion by means of a high-frequency plasma emission spectral analysis method. The crystal was identified as a complex crystal comprising pyrazinophenanthroline, the anion of triiodine and the iron ion by means of an X-ray diffraction (shown as FIG. 4). The complex crystal comprised 2 parts of the cation of pyrazinophenanthroline, 1 part of $I_3^-$, and 0.026 parts of the metal ion.

0.1 g of the obtained complex crystal and 0.1 g of cellulose nitrate were dissolved into a mixed solution comprising 7 g of acetone and 10 g of ethanol to prepare a solution. 10 g of ditridecyl phthalate (DTDP) was added to the solution, and aceton and ethanol were distilled under reduced pressure to precipitate a microcrystal of the complex in DTDP. The DTDP solution was treated by the ultrasonic cleaner for 10 hours, and after that, remaining aceton and ethanol were removed under reduced pressure. Particles which were not refined satisfactorily were precipitated and removed by a centrifugal separation treatment (18,000 rpm, 20 minutes), thereby obtaining a purple suspension in which the complex crystal was dispersed into DTDP.

The purple suspension was sealed in glass cell having a gap of 100 μm, and tested for a weather resistance by a sunshine weather-O-meter for 240 hours. As a result, the color and the dispersed state of the purple suspension never changed.

Third Preferred Embodiment

A Third Preferred Embodiment employed pyrazinophenanthroline to obtain a metal ion coordinated complex crystal as follows.

1.30 g (5.6 millimol) of pyrazinophenanthroline (shown as structural formula 2) was dissolved into a mixed solution comprising 36 g of water and 0.13 g of concentrated sulfuric acid and stirred to prepare a solution (A). 0.711 g of iodine, 0.465 g of potassium iodide and 26.8 mg of copper sulfate (3 mol % per pyrazino phenanthroline) were dissolved into a mixed solution comprising 15.0 g of water and 3.5 g of ethanol to prepare a solution (B). The solutions (A) and (B) were mixed at once and stirred for 1 hour to form a precipitate. The precipitate was filtered and then vacuum dried to obtain a metal ion coordinated complex crystal.

The complex crystal was identified to contain 0.43 atomic % of copper ion by means of a high-frequency plasma emission spectral analysis method. The crystal was identified as a complex crystal comprising pyrazino phenanthroline, the anion of triiodine and the copper ion by means of an X-ray diffraction (shown as FIG. 5). The complex crystal comprised 2 parts of the cation of pyrazino phenanthroline, 1 part of $I_3^-$, and 0.023 parts of the metal ion.

0.1 g of the obtained complex crystal and 0.1 g of cellulose nitrate were dissolved into a mixed solution comprising 7 g of acetone and log of ethanol to prepare a solution. 10 g of ditridecyl phthalate (DTDP) was added to the solution, and aceton and ethanol were distilled under reduced pressure to precipitate a microcrystal of the complex in DTDP. The DTDP solution was treated by the ultrasonic cleaner for 10 hours, and after that, remaining aceton and ethanol were removed under reduced pressure. Particles which were not refined satisfactorily were precipitated and removed by a centrifugal separation treatment (18,000 rpm, 20 minutes), thereby obtaining a purple suspension in which the complex crystal was dispersed into DTDP.

The purple suspension was sealed in glass cell having a gap of 100 μm, and tested for a weather resistance by a sunshine weather-O-meter for 240 hours. As a result, the color and the dispersed state of the purple suspension never changed.

Fourth Preferred Embodiment

A Fourth Preferred Embodiment employed pyrazinophenanthroline to obtain a metal ion coordinated complex crystal as follows.

1.30 g (5.6 millimol) of pyrazinophenanthroline (shown as structural formula 2) was dissolved into a mixed solution comprising 36 g of water and 0.13 g of concentrated sulfuric acid and stirred to prepare a solution (A). 0.711 g of iodine, 0.465 g of potassium iodide and 26.0 mg of nickel sulfate (3 mol % per pyrazinophenanthroline) were dissolved into a mixed solution comprising 15.0 g of water and 3.5 g of ethanol and stirred to prepare a solution (B). The solutions (A) and (B) were mixed at once and stirred for 1 hour to form a precipitate. The precipitate was filtered and then vacuum dried to obtain a metal ion coordinated complex crystal.

The complex crystal was identified to contain 0.44 atomic % of nickel ion by means of a high-frequency plasma emission spectral analysis method. The crystal was identified as a complex crystal comprising pyrazinophenanthroline, the anion of triiodine and the nickel ion by means of an X-ray diffraction (shown as FIG. 6). The complex crystal comprised 2 parts of the cation of pyrazino phenanthroline, 1 part of $I_3^-$, and 0.064 parts of the metal ion.

0.1 g of the obtained complex crystal and 0.1 g of cellulose nitrate were dissolved into a mixed solution comprising 7 g of acetone and 10 g of ethanol to prepare a solution. 10 g of ditridecyl phthalate (DTDP) was added to the solution, and aceton and ethanol were distilled under reduced pressure to precipitate a microcrystal of the complex in DTDP. The DTDP solution was treated by the ultrasonic cleaner for 10 hours, and after that, remaining aceton and ethanol were removed under reduced pressure. Particles which were not refined satisfactorily were precipitated and removed by a centrifugal separation treatment (18,000 rpm, 20 minutes), thereby obtaining a purple suspension in which the complex crystal was dispersed into DTDP.

The purple suspension was sealed in glass cell having a gap of 100 μm, and tested for a weather resistance by a sunshine weather-O-meter for 240 hours. As a result, the color and the dispersed state of the purple suspension never changed.

Comparative Example

A Comparative Example employed 1,10-phenanthroline to obtain a complex crystal as follows.

1.01 g (5.6 millimol) of 1,10-phenanthroline (shown as structural formula 1) was dissolved into a mixed solution comprising 21 g of water and 0.137 g of concentrated sulfuric acid and stirred to prepare a solution (A). 0.711 g of iodine and 0.465 g of potassium iodide were dissolved into a mixed solution comprising 14.0 g of water and 3.5 g of ethanol and stirred to prepare a solution (B). The solutions (A) and (B) were mixed at once and stirred for 1 hour to form a precipitate. The precipitate was filtered and then vacuum dried to obtain a complex crystal. 0.1 g of the obtained complex crystal and 0.1 g of cellulose nitrate were dissolved into a mixed solution comprising 7 g of acetone and log of ethanol to prepare a solution. 10 g of ditridecyl phthalate (DTDP) was added to the solution, and aceton and ethanol were distilled under reduced pressure to precipitate a microcrystal of the complex in DTDP. The DTDP solution was treated by the ultrasonic cleaner for 10 hours, and after that, remaining aceton and ethanol were removed under reduced pressure. Particles which were not refined satisfactorily were precipitated and removed by a centrifugal separation treatment (18,000 rpm, 20 minutes), thereby obtaining a blue suspension in which the complex crystal was dispersed into DTDP.

Figure 7:
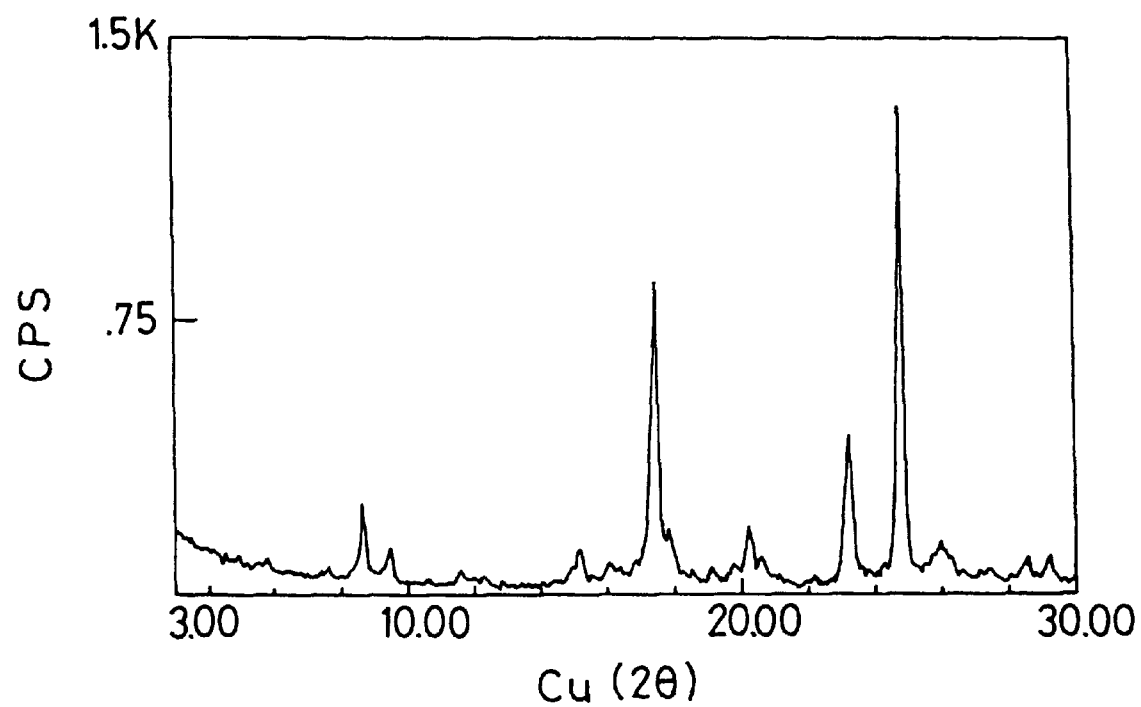
FIG. 7 is an X-ray chart of the complex crystal in the Comparative Example.

The crystal was identified as a complex crystal comprising 1,10-phenanthroline and the anion of triiodine by means of an X-ray diffraction (shown as FIG. 7). The complex crystal comprised 7 parts of the cation of 1,10-phenanthroline and 3 parts of $I_3^-$.

The blue suspension was sealed in glass cell having a gap of 100 μm, and tested for a weather resistance by a sunshine weather-O-meter for 240 hours. As a result, the color of the blue suspension remarkably faded because the metal ion was not coordinated.

The metal ion coordinated complex crystals of the present embodiments have the following features and effects. The complex crystal comprises a nitrogen-containing heterocyclic aromatic compound, periodic acid, and a metal ion which is coordinated with the nitrogen-containing heterocyclic aromatic compound. The complex crystal forms a charge-transfer complex, has polarizability, and property of light-polarizing particles in the same manner as the complex crystal comprising a nitrogen-containing heterocyclic aromatic compound and periodic acid. The complex crystal absorbs light such as ultra violet, and the ultra violet is converted into heat to be emitted. So, the complex crystal is not subjected to deterioration caused by light. Furthermore, the complex crystal is not subjected to heat deterioration because it is thermally stable. As a result, the complex crystal can improve not only its heat resistance but also its weather resistance.

Light-polarizing particles made of the above complex crystal hardly deteriorate due to ultra violet, and have improved in weather resistance. As a result, it is possible to prevent the particles in the suspension from aggregation or changing colors caused by ultra violet.

What is claimed is:

1. A metal ion coordination complex crystal comprising:
   a protonated derivative of a compound containing at least one basic nitrogen and an aromatic heterocyclic ring wherein said nitrogen is optionally in the heterocyclic ring;
   an anion of triiodine;
   a positive metal ion coordinated by nitrogen; and
   optionally an anion of an acid other than triiodine.

2. The metal coordination complex crystal of claim 1, further comprising said compound in unprotonated form.

3. A metal ion coordination complex crystal according to claim 1, wherein said compound is a polycyclic compound comprising at least one aromatic ring.

4. A metal ion coordination complex crystal according to claim 3, wherein said protonated derivative has at least one fused aromatic ring.

5. A metal ion coordination complex crystal according to claim 4, wherein said protonated derivative has a fused aromatic ring system having 3 to 5 rings.

6. A metal ion coordination complex crystal according to claim 4, wherein said compound is 1,10-phenanthroline, pyrazinophenanthroline, dipyridophenazine, 5-methoxyphenanthroline, 5-aminophenanthroline or diphenylphenanthroline.

7. A metal ion coordination complex crystal according to claim 4, wherein said compound is 1,10-phenanthroline.

8. A metal ion coordination complex crystal according to claim 4, wherein said compound is pyrazinophenanthroline or dipyridophenazine.

9. A metal ion coordination complex crystal according to claim 4, wherein said compound is 5-methoxyphenanthroline, 5-aminophenanthroline or diphenylphenanthroline.

10. A metal ion coordination complex crystal according to claim 1, wherein said complex crystal comprises protonated and unprotonated 1,10-phenanthroline; anions of triiodine; and copper ions; and
    the molar ratio of:
    the total of said protonated and unprotonated 1,10 phenanthroline, to
    said anions of triiodine, to
    said copper ions,
    is 7:3:0.06.

11. A metal ion coordination complex crystal according to claim 2, wherein said complex crystal comprises protonated and unprotonated pyrazinophenanthroline; anions of triiodine; and iron ions; and the molar ratio of:
the total of said protonated and unprotonated pyrazinophenanthroline, to
said anions of triiodine, to
said iron ions,
is 2:1:0.026.

12. A metal ion coordination complex crystal according to claim 2, wherein said complex crystal comprises protonated and unprotonated pyrazinophenanthroline; anions of triiodine; and copper ions; and the molar ratio of:
the total of said protonated and unprotonated pyrazinophenanthroline, to
said anions of triiodine, to
said copper ions,
is 2:1:0.023.

13. A metal ion coordination complex crystal according to claim 2, wherein said complex crystal comprises protonated and unprotonated pyrazinophenanthroline; anions of triiodine; and nickel ions; and the molar ratio of:
the total of said protonated and unprotonated pyrazinophenanthroline to
said anions of triiodine, to
said nickel ions,
is 2:1:0.064.

14. A metal ion coordination complex crystal according to claim 1, wherein said metal ion is a transition metal ion.

15. A metal ion coordination complex crystal according to claim 14, wherein said transition metal ion is an ion of at least one metal selected from the group consisting of copper, iron or nickel.

16. A metal ion coordination complex crystal according to claim 1, wherein said compound has a substituent selected from the group consisting of an amino group, hydrazide group, or guanidyl group.

17. A metal ion coordination complex crystal according to claim 1, wherein said compound has an aromatic hydrocarbon substituent.

18. A metal ion coordination complex crystal according to claim 17, wherein said aromatic hydrocarbon substituent is a diphenyl group.

19. A metal ion coordination complex crystal according to claim 1, wherein said compound has an alkoxy or phenoxy substituent.

20. A metal ion coordination complex crystal according to claim 19, wherein said substituent is at least one selected from the group consisting of a methoxy group, ethoxy group or phenoxy group.

21. A metal ion coordination complex crystal according to claim 1, further comprising an acid.

22. A metal ion coordination complex crystal according to claim 1, wherein said compound has a substituent and said substituent is at least one selected from the group consisting of a methylthio group, ethylthio group or phenylthio group.

23. A metal ion coordination complex crystal according to claim 1, wherein said compound has a halogen substituent.

24. A metal ion coordination complex crystal according to claim 1, wherein said compound has an aliphatic hydrocarbon substituent having less than 10 carbons.

25. A metal ion coordination complex crystal according to claim 21, wherein said acid is an inorganic acid.

26. A metal ion coordination complex crystal according to claim 25, wherein said inorganic acid is a strong acid.

27. A metal ion coordination complex crystal according to claim 25, wherein said inorganic acid is at least one selected from the group consisting of hydrochloric acid, sulfuric acid, phosphoric acid or hydroiodic acid.

28. A metal ion coordination complex crystal according to claim 21, wherein said acid is an organic acid.

29. A metal ion coordination complex crystal according to claim 28, wherein said organic acid is at least one selected from the group consisting of a monocarboxylic acid, dicarboxylic acid or sulfonic acid, said sulfonic acid is at least one selected from the group consisting of a benzenesulfonic acid, toluenesulfonic acid and methanesulfonic acid said monocarboxylic acid is at least one selected from the group consisting of an acetic acid, propionic acid, butyric acid, valeric acid, trifluoroacetic acid and benzoic acid, and said dicarboxylic acid is at least one selected from the group consisting of an oxalic acid, malonic acid, maleic acid, fumaric acid and phthalic acid.

* * * * *